United States Patent [19]

Bolin et al.

[11] Patent Number: 6,080,837
[45] Date of Patent: Jun. 27, 2000

[54] SYNTHESIS OF VIP ANALOG

[75] Inventors: David Robert Bolin, Montclair; Waleed Danho, Wayne; Arthur M. Felix, West Caldwell, all of N.J.

[73] Assignee: Hoffmann-La Roche Inc., Nutley, N.J.

[21] Appl. No.: 08/798,394

[22] Filed: Feb. 7, 1997

(Under 37 CFR 1.47)

Related U.S. Application Data

[60] Provisional application No. 60/011,425, Feb. 9, 1996.
[51] Int. Cl.[7] ............................... C07K 1/10; C07K 14/00
[52] U.S. Cl. ........................... 530/324; 530/334; 530/338
[58] Field of Search ...................................... 530/333, 334, 530/338, 324, 327, 328, 329, 326

[56] References Cited

U.S. PATENT DOCUMENTS 4,237,046  12/1980  Bodanszky et al. .

FOREIGN PATENT DOCUMENTS

| 536741 | 4/1993 | European Pat. Off. . |
|---|---|---|
| 0 606 816 | 7/1994 | European Pat. Off. . |
| 91/04041 | 4/1991 | WIPO . |

OTHER PUBLICATIONS

Chemical Abstracts, vol. 101, No. 19, Nov. 5, 1984, abstract No. 171691.

Paul, et al. J. Biol Chem. Site Specificity of a Catalytic Vasoactive Intestinal Peptide Antibody. 265:11910–11913 (1990).

Remmer et al., 'Comparison of FMOC Solid Phase Methods for Teh Synthesis of Pure [Nle 17]–VIP', Innovation Perspect. Sold Phayse Synth. Collect. Pap. Int. Symp., 3rd (1994), Meedtin date 1993. (Ed. Epton, Roger). Mayflower Worldwide Ltd., Brimingham, UK, 1994.

Jaeger et al., 'Structre Activity Studies on VIP. II. Synthesis of Analogs Modified at Position Arg 12, Arg 14–Lys 15, Met 17 and Lys 20–Lys 21, Including a Potent VIP/PHM–Hybrid', Int.Symp. Vasoact. Intest. Pept., Pituitary Adenylate Cyclase Act. Polypept, 1994.

O'Dennell et al., 'Ro 25–1553: A Novel, Long–Acting Vasoactive Intestinal Peptide Agonist. Part 1: In Vitro and In Vivo Brochodilator Studies', Journal of Pharmacology and Experimental Therapeutics, vol. 270, No. 3, pp. 1282–1288, 1994.

Primary Examiner—Cecillia J. Tsang
Assistant Examiner—Anish Gupta
Attorney, Agent, or Firm—George W. Johnston; William H. Epstein; Briana C. Buchholz

[57] ABSTRACT

This invention relates to a novel process for the synthesis of vasoactive intestinal peptide analog Ac(1–31)—$NH_2$ from four protected peptide fragments.

9 Claims, No Drawings

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 31 amino acids
      (B) TYPE: amino acid
      (C) STRANDEDNESS: single
      (D) TOPOLOGY: linear (ii) MOLECULE TYPE: peptide (iii) HYPOTHETICAL: NO (ix) FEATURE:
      (A) NAME/KEY: Modified-site
      (B) LOCATION: 21..25
      (D) OTHER INFORMATION: /note= "SIDE CHAIN CYCLIZATION AT
         LYS21 TO ASP25"

(xi) SEQUENCE DESCRIPTION: SEQ ID NO:1:

```
His Ser Asp Ala Val Phe Thr Glu Asn Tyr Thr Lys Leu Arg Lys Gln
1               5                   10                  15

Xaa Ala Ala Lys Lys Tyr Leu Asn Asp Leu Lys Lys Gly Gly Thr
            20                  25                  30
```

(2) INFORMATION FOR SEQ ID NO:2:

(i) SEQUENCE CHARACTERISTICS:
      (A) LENGTH: 6 amino acids
      (B) TYPE: amino acid
      (C) STRANDEDNESS: single
      (D) TOPOLOGY: linear (ii) MOLECULE TYPE: peptide (iii) HYPOTHETICAL: NO (xi) SEQUENCE DESCRIPTION: SEQ ID NO:2:

```
Leu Lys Lys Gly Gly Thr
1               5
```

```
(2) INFORMATION FOR SEQ ID NO:3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 3..7
        (D) OTHER INFORMATION: /note= "SIDE CHAINS OF LYS3 AND
            ASP7 ARE CYCLIZED"

(xi) SEQUENCE DESCRIPTION: SEQ ID NO:3:

Ala Lys Lys Tyr Leu Asn Asp
1               5

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:4:

Asn Tyr Thr Lys Leu Arg Lys Gln Xaa Ala
1               5                   10

(2) INFORMATION FOR SEQ ID NO:5:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:5:

His Ser Asp Ala Val Phe Thr Glu
1               5

(2) INFORMATION FOR SEQ ID NO:6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (iii) HYPOTHETICAL: NO (ix) FEATURE:
        (A) NAME/KEY: Modified-site
        (B) LOCATION: 3..7
        (D) OTHER INFORMATION: /note= "SIDE CHAINS OF LYS3 AND
            ASP7 ARE CYCLIZED"
```

-continued (xi) SEQUENCE DESCRIPTION: SEQ ID NO:6:

Ala Lys Lys Tyr Leu Asn Asp Leu Lys Lys Gly Gly Thr
1               5                  10

(2) INFORMATION FOR SEQ ID NO:7:

(i) SEQUENCE CHARACTERISTICS:
        (A) LENGTH: 23 amino acids
        (B) TYPE: amino acid
        (C) STRANDEDNESS: single
        (D) TOPOLOGY: linear (ii) MOLECULE TYPE: peptide (iii) HYPOTHETICAL: NO (xi) SEQUENCE DESCRIPTION: SEQ ID NO:7:

Asn Tyr Thr Lys Leu Arg Lys Gln Xaa Ala Ala Lys Lys Tyr Leu Asn
1               5                   10                  15

Asp Leu Lys Lys Gly Gly Thr
                20

SYNTHESIS OF VIP ANALOG

This application claims benefit of Provisional Appl. No. 60/011,425 filed Feb. 9, 1996.

TECHNICAL FIELD

This invention relates to a novel process for the synthesis of vasoactive intestinal peptide analog Ac(1–31)—NH$_2$ from four protected peptide fragments.

BACKGROUND OF THE INVENTION

Vasoactive intestinal peptide (VIP) is a smooth muscle relaxant/bronchodilator which regulates airway mucus secretion and has anti-allergic and anti-inflammatory properties. Recent studies have resulted in the discovery of an analog of VIP which possesses enhanced metabolic stability and has increased receptor-binding properties. This VIP analog is the subject of a co-pending U.S. patent application Ser. No. 08/308,729.

To date, this VIP analog has been prepared using solid phase synthesis. The solid phase synthesis includes attaching an alpha-amino acid, protecting with, for example t-butyloxycarbonyl (Boc), by ester linkage, to a chloromethylated resin or a hydroxymethyl resin. More amino acids are added sequentially to the resin. The alpha amino Boc protection is removed under acidic conditions and the subsequent protected amino acids are coupled stepwise to obtain an intermediate, protected peptide-resin. Blocking groups are removed and the peptide is cleaved from the resin through multiple hydrogen fluoride cleavage reactions. Purification of the peptides occurs in two stages, a) size exclusion gel chromatography and b) preparative high performance liquid chromatography (HPLC). This multistep process is time consuming and results in inefficient recovery of the target peptide.

It is thus an object of the present invention to provide a relatively simple, more efficient and economic procedure for the synthesis of the VIP analog.

SUMMARY OF THE INVENTION

The present invention provides a novel process for the synthesis of a VIP analog, AC(1–31)—NH$_2$, having the formula (SEQ ID NO: 1)

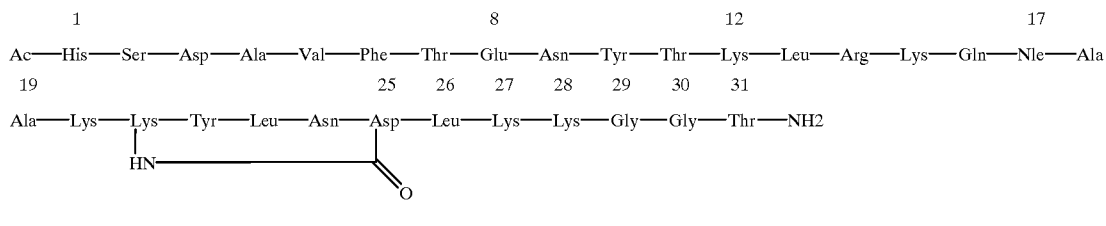

from four protected peptide fragments. The novel process according to the present invention does not require prior preparative HPLC purification of the peptide fragments as is required when the analog is prepared by solid phase synthesis, nor does it require purification of the intermediates formed during the synthesis of the target cyclic VIP analog. The resulting product was purified in the final stage after assembly by a single pass via preparative HPLC.

DETAILED DESCRIPTION OF THE INVENTION

The method of the present invention for the synthesis of the cyclic VIP analog Ac—(1–31)—NH$_2$ comprises the repetitive assemblage of four protected peptide fragments: Fragment I, Fmoc-(26–31)—NH$_2$ (SEQ ID NO: 2); Fragment II, Fmoc-(19–25)—OH (SEQ ID NO:3); Fragment III, Fmoc-(9–18)—OH (SEQ ID NO:4); and Fragment IV, Ac—(1–8)—OH (SEQ ID NO:5), each of which is shown below.

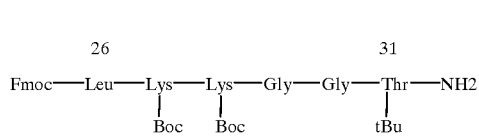

(I)

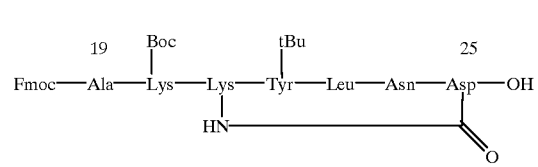

(II)

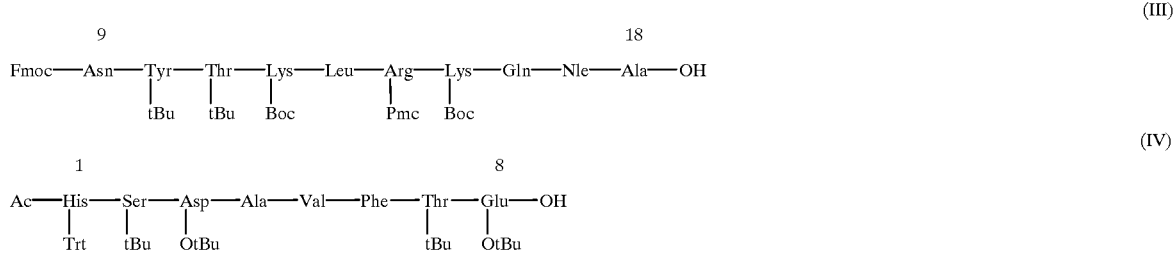

(III)

(IV)

The method of the present invention for the synthesis of a compound Ac—(1–31)—$NH_2$ (SEQ ID NO:1) by coupling four Fmoc protected peptide fragments, peptide Fragment I (SEQ ID NO:2), peptide Fragment II (SEQ ID NO:3), peptide Fragment III (SEQ ID NO: IV) and peptide Fragment IV (SEQ ID NO:5) comprises
  (a) deprotecting the Fmoc-protecting group of peptide Fragment I and coupling the deprotected peptide Fragment I with protected peptide Fragment II; (b) deprotecting the Fmoc-protecting group of the resulting peptide of step (a) and coupling it with protected Fragment III; (c) deprotecting the Fmoc-protecting group of the resulting peptide of step (b) and coupling it with protected Fragment IV; (d) deprotecting the resulting protected peptide of step (c) to yield deprotected Ac(1–31)—$NH_2$.

The protected peptide fragments I–IV were selected on the basis of maximum coupling efficiency and minimal racemization of the product of each coupling reaction. Equivalent amounts of each fragment were used for each coupling reaction, providing an economic pathway to the target peptide. The intermediates formed after each coupling were used directly for subsequent coupling reactions without further purification.

The purity of each fragment produced after solid phase synthesis, as described herein, was from about 82% to about 97% after a single purification step as determined by analytical HPLC, and each fragment was used for the synthesis of the cyclic VIP analog without further purification.

More particularly the method for the synthesis of the purified compound of the formula Ac—(1–31)—$NH_2$ (SEQ ID NO:1) comprises: (a) deprotecting the Fmoc-protecting group of peptide Fragment I (SEQ ID NO:2) and coupling the deprotected peptide Fragment I with protected peptide Fragment II (SEQ ID NO:3) yielding protected intermediate peptide Fmoc(19–31)—$NH_2$ (SEQ ID NO:6); (b) deprotecting the Fmoc-protecting group of intermediate Fmoc(19–31)—$NH_2$ and coupling the deprotected intermediate Fmoc (19–31)—NH2 with protected Fragment III (SEQ ID NO: IV) yielding protected intermediate peptide Fmoc(9–31)—$NH_2$ (SEQ ID NO:7); (c) deprotecting the Fmoc-protecting group of intermediate Fmoc(9–31)—$NH_2$ and coupling the deprotected intermediate Fmoc(9–31)—$NH_2$ with protected Fragment IV (SEQ ID NO:5) yielding protected intermediate peptide Ac—(1–31)—$NH_2$; (d) deprotecting the protected peptide Ac(1–31)—$NH_2$; and (e) purifying the deprotected peptide Ac(1–31)—$NH_2$, for example, via preparative HPLC.

As used herein, the nomenclature used to define the peptides is that typically used in the art, wherein the amino group at the N-terminus appears to the left and the carboxyl group at the C-terminus appears to the right. By natural amino acids is meant one of the naturally occurring amino acids found in proteins, i.e., Gly, Ala, Val, Leu, Ile, Ser, Thr, Lys, Arg, Asp, Asn, Glu, Gln, Cys, Met, Phe, Tyr, Pro, Trp, and His. Where the amino acid has isomeric forms, it is the L form of the amino acid that is represented, unless otherwise expressly indicated.

The following abbreviations or symbols are used to represent amino acids in addition to those described elsewhere herein, protecting groups, solvents, reagents and the like.

| Symbol | Meaning |
| --- | --- |
| Ac | Acetyl |
| Nle | Norleucine |
| Fm | 9-Fluorenylmethyl |
| DIPEA | N,N-Diisopropylethylamine |
| DMF | Dimethylformamide |

The suffixes "—OH" and "—$NH_2$" following "VIP" refer to the free acid and amide forms of the polypeptide, respectively. In the event neither suffix is used, the expression is intended to encompass both forms.

A cyclic peptide, as defined herein, is a peptide wherein the side chain carboxy terminus of one amino acid in the peptide is attached covalently to the side chain amino terminus of another amino acid in the peptide chain via formation of an amide bond. Several nomenclatures and symbols are utilized to represent a cyclic peptide. The following are examples:
  a. cyclo($Lys^{21}$—$Asp^{25}$)-Fmoc-$Ala^{19}$—$Lys(Boc)^{20}$—$Lys^{21}$—$Tyr(tBu)^{22}$—$Leu^{23}$—$Asn^{24}$—$Asp^{25}$—OH;
  b. Fmoc-(19–25)—OH;
  c. Fmoc-[$Ala^{19}$—$Asp^{25}$]-VIP cyclo(21→25);
  d. [Fmoc-(SEQ ID NO:3)—OH];
  e. Fmoc-[$Ala^{19}$—$Asp^{25}$]-VIP cyclo ($Lys^{21}$→$Asp^{25}$);
  f. [Fmoc-(SEQ ID NO:3)—OH];
  g.

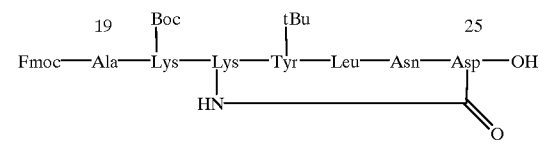

The above structures (a–g), and the representation using the "(SEQ ID NO:)" each represent and define the same peptide having an amino acid sequence corresponding to a VIP peptide fragment in which an Fmoc group has been substituted for hydrogen at the N-terminus. Additionally, an amide bond has been formed between the side chain amine of the lysine at position 21 and the side chain carboxyl of aspartic acid at position 25, thus forming the cyclic peptide fragment. The above representations for the peptide structure are considered to be equivalent and interchangeable.

In the cyclic peptides of the present invention, the following configurations apply unless otherwise stated.

| Amino Acid in chain | Terminus of amino acid bound to make cyclic peptide |
|---|---|
| Lys | ε amino ε |
| Asp | β carboxyl (β = beta) |
| Glu | γ carboxyl (γ = gamma) |

The peptide fragments which comprise the VIP analog of the present invention may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group or other reactive groups protected and the free primary carboxyl group of another amino acid or residue thereof having its amino group or other reactive groups protected.

The process for synthesizing the peptide fragments comprising the VIP analog may be carried out by a procedure whereby each amino acid in the desired sequence is added one at a time in succession to another amino acid or residue thereof or by a procedure whereby peptide fragments with the desired amino acid sequence are first synthesized conventionally and then condensed to provide the desired peptide.

Such conventional procedures for synthesizing the peptide fragments include, for example, any solid phase peptide synthesis method. In such a method, the synthesis of the peptide fragments can be carried out by sequentially incorporating the desired amino acid residues one at a time into the growing peptide chain according to the general principles of solid phase methods [Merrifield, R. B., J. Amer. Chem. Soc. 85, 2149–2154 (1963); Barany et al., The Peptides, Analysis, Synthesis and Biology, Vol. 2, Gross, E. and Meienhofer, J., Eds. Academic Press 1–284 (1980)].

Common to chemical syntheses of peptides is the protection of reactive side chain groups of the various amino acid moieties with suitable protecting groups which will prevent a chemical reaction from occurring at that site until the protecting group is ultimately removed. It is also well known to protect the alpha amino group on an amino acid or fragment while that entity reacts at the carboxyl group, followed by the selective removal of the alpha amino protection group to allow a subsequent reaction to take place at that site. While specific protecting groups have been disclosed in regard to the solid phase synthesis method, it should be noted that each amino acid can be protected by a protective group conventionally used for the respective amino acid in solution phase synthesis.

Alpha amino groups may be protected by a suitable protecting group selected from aromatic urethane-type protecting groups, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenyl-methyl-oxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Boc is most preferred for alpha amino protection.

Carboxyl groups may be protected by a suitable protecting group selected from aromatic esters such as benzyl (OBzl) or benzyl substituted with lower alkyl, halo, nitro, thio, or substituted thio, i.e., lower alkyl (1–7 carbon atoms), thio, aliphatic esters such as lower alkyl, t-butyl (Ot—Bu), cyclopentyl, cyclohexyl (OcHx), cycloheptyl, and 9-fluorenylmethyl (OFm). OBzl and OFm are most preferred for glumatic acid (Glu). OChx, OBzl and OFm are most preferred for aspartic aid (Asp).

Hydroxyl groups may be protected by a suitable protecting group selected from ethers such as benzyl (Bzl) or benzyl substituted with lower alkyl, halo, such as 2,6-dichlorobenzyl (DCB), nitro, or methoxy; t-butyl (t-Bu), tetrahydropyranyl, and triphenylmethyl (trityl). Bzl is most preferred for serine (Ser) and threonine (Thr). Bzl and DCB are most preferred for tyrosine (Tyr).

Side chain amino groups may be protected by a suitable protecting group selected from aromatic urethane-type protecting groups such as benzyloxycarbonyl (Z) and substituted benzyloxycarbonyl, such as p-chlorobenzyloxycarbonyl, 2-chlorobenzyloxycarbonyl, (2-Cl-Z), p-nitro-benzyloxycarbonyl, p-bromobenzyloxycarbonyl, p-biphenyl-isopropyl-oxycarbonyl, 9-fluorenylmethyloxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Z is most preferred for ornithine (Orn). 2-Cl-Z and Fmoc are most preferred for lysine (Lys).

Guanidino groups may be protected by a suitable protecting group selected from nitro, p-toluenesulfonyl (Tos), Z, adamantyloxycarbonyl, and Boc. Tos is most preferred for arginine (Arg).

Side chain amide groups may be protected by xanthyl (Xan). No protection is preferred for asparagine (Asn) and glutamine (Gln).

Imidazole groups may be protected by a suitable protecting group selected from p-toluenesulfonyl (Tos), 9-fluorenylmethyloxycarbonyl (Fmoc), triphenylmethyl (trityl), 2,4-dinitrophenyl (Dnp), Boc and benzyloxymethyl (Bom). Tos and Bom are most preferred for histidine (His).

A protected amino acid may be represented for purposes of the present invention, for example, as Lys(Boc), Glu (OtBu), and Tyr(tBu).

All solvents including methanol (MeOH), methylene chloride ($CH_2Cl_2$), acetonitrile ($CH_3CN$), ether, hexane and dimethylformamide (DMF) were purchased from Fisher or Burdick and Jackson. Trifluoroacetic acid (TFA) was purchased from Halocarbon and used without further purification. Diisopropylethylamine (DIPEA), 1,2-ethanedithiol (EDT), dicyclohexylcarbodiimide (DCC), N-hydroxy-succinimide (HOSu) and thioanisole were purchased from Aldrich Chemical Co., Inc. (Milwaukee, Wis.) 1-Hydroxybenzotriazole (HOBT) was purchased from Sigma Chemical Co. (St. Louis, Mo.), [2-(1 H-benzotriazol-1-yl)-1,1,3,3-tetramethyluronium hexafluorophosphate (HBTU) and benzotriazol-1-yloxy-tri-(dimethylamino)-phosphonium hexafluorophosphate (BOP) were purchased from Richelieu Biotechnologies (St. Hyacinthe, Quebec, Canada). 2-Methoxy-4-alkoxybenzyl alcohol copolystyrene 1% divinylbenzene (Sasrin-resin) was obtained from Bachem Bioscience. Fmoc/tBu-protected amino acids were all of the L-configuration and were purchased form Bachem, Inc. (Torrance, Calif.).

Analytical high performance liquid chromatography (HPLC) was carried out on an LDC Constametric IIG equipped with a Gradient Master and spectromonitor III UV-Variable Wavelength Detector and performed on a Lichrosorb RP-8 (5µ) column (4.6 mm×25 cm); Eluant: (A) 0.1 M NaClO$_4$ (pH 2.5)-(B) CH$_3$CN with a linear gradient in 20 minutes; Flow 1 ml/minute; Detection 214 nm. HPLC of the protected intermediates, Fmoc-(19–31)-NH$_2$ and Fmoc-(9–31)-NH$_2$, was performed on a Lichrosorb RP-8 (5µ) column (4.6 mm×25 cm); eluant: (A) NaClO$_4$ (pH 2.5)-(B) CH$_3$CN; linear gradient 40–90% (B) in 20 minutes; flow 1 ml/minute; detection 214 nm. HPLC of protected Ac-(1–31)-NH$_2$ was carried out on the same column using (B) CH$_3$CN:IPrOH (1:1); linear gradient 60–95% (B) in 20 minutes. HPLC of the cyclic VIP analog was performed on (i) a Vydac C-18 column; eluant: (A) H$_2$O (0.1% TFA)-(B) CH$_3$CN (0.1% TFA); linear gradient 15–30% (B) in 20 minutes; flow 1 ml/minute; detection 214 nm (ii) a Zorbax Protein Plus column; eluant: (A) H$_2$O (0.1% TFA)- (B) CH$_3$CN (0.1% TFA); linear gradient 20–35% (B) in 20 minutes; flow 2 ml/minute; detection 210 nm (iii) a Lichrosorb RP-8 (5µ) column; eluant: (A) NaClO$_4$ (pH 2.5)-(B) CH$_3$CN; linear gradient 30%–50% (B) in 20 minutes; flow 1 ml/minute; detection 206 nm. Preparative HPLC was carried out on a Delta Prep 3000 system YMC ODS-A (120Å, 15µ) column (4.7×50 cm); eluant (A) H$_2$O (0.1% TFA)- (B) CH$_3$CN:MeOH (1:1) (0.1% TFA); linear gradient 20–50% (B) in 3 h; flow 80 ml/minute; detection 215 nm.

Fast atom bombardment mass spectra (FAB-MS) were recorded on a Beckman VG2AB-1F or VG70E-HF mass spectrometer. Amino acid analyses were performed on a Beckman Model 121 M Amino Acid Analyzer. The protected peptide fragment and free peptides were hydrolyzed in 6 N HCl (Pierce Chemical Co.) in sealed, evacuated tubes at 110° C. for 24 h.

In the present invention, the four peptide fragments I–IV were prepared via repetitive solid phase synthesis. Coupling reactions throughout the syntheses were monitored by the Kaiser ninhydrin test to determine reaction progress and completion. (Kaiser et al., Anal. Biochem., 34, 595–598 (1970). Preparation of the resins was monitored by UV analysis as follows:

The substitution of a protected amino acid (AA) resin (Fmoc-AA-resin) at any point in the synthesis procedure uses the absorbance of N-(9-fluorenylmethyl) piperidine at 301 nm ($\epsilon$=7800). Between 4 to 8 mg of resin is accurately weighed in a test tube and treated with 0.5 ml of 20% piperidine in DMF. For example, into a test tube containing 5.05 mg of Fmoc-Gly-resin, 0.5 ml 20% piperidine in DMF is added. 0.5 ml 20% piperidine in DMF in an empty test tube is used as a blank. Over the next 15 minutes, the test tube with the Fmoc-Gly-resin is swirled two or three times to make sure all the resin has come into contact with the piperidine solution. DMF is added to both tubes to bring the volume to 50 ml. The spectrophotometer is zeroed at 301 nm with the blank. The absorbance of the Fmoc-substitution is calculated as follows:

$$\frac{A301 \times \text{Vol(ml)}}{7800 \times \text{wt(g)}} = \frac{526 \times (50)}{7800 \times .00505(g)} = 0.67\,\text{mmol/g.}$$

Generally, deprotection of the Fmoc protecting group from the peptide resin fragments was conducted acording to the following procedure:

| Protocol 1: Fmoc-Deprotection | | |
|---|---|---|
| Step | Reagents | Time |
| 1 | CH$_2$Cl$_2$ | 2 × 3 |
| 2 | DMF | 3 minutes |
| 3 | 25% Piperidine | 5 minutes |
| 4 | 25% Piperidine | 15 minutes |
| 5 | DMF | 3 minutes |
| 6 | MeOH | 3 minutes |
| 7 | CH$_2$Cl$_2$ | 3 minutes |
| 8 | MeOH | 3 minutes |
| 9 | CH$_2$Cl$_2$ | 3 × 3 minutes |
| 10 | DMF | 3 minutes |
| 11 | Coupling | 90 minutes |
| 12 | DMF | 3 minutes |
| 13 | MeOH | 3 minutes |
| 14 | CH$_2$Cl$_2$ | 3 minutes |
| 15 | MeOH | 2 × 3 minutes |

The synthesis of Fragment I, Fmoc-(26–31)-NH$_2$, described in Examples 1 to 8, included preparing a C-terminus amide fragment using an XAL-linker resin and using benzotriazol-1-yloxytris-(dimethylamino) phosphonium hexafluorophosphate (BOP) as the coupling reagent. Generally, double coupling was performed for each amino acid to ensure final purity. Typically, four equivalents of reagents were used for the first coupling and two equivalents of reagents were used for the second coupling.

The synthesis of Fragment II, Fmoc-(19–25)-OH, described in Examples 9 to 15, comprised a stepwise solid phase assemblage of the protected heptapeptide in which the COOH-terminal residue, Asp, was linked to Sasrin-resin at the β-COOH via Fmoc-Asp(O-Sasrin)-OBzl. The starting resin was coupled with the dipeptide, Fmoc-Leu—Asn—OH which was prepared from Fmoc-Leu—OH and H-Asn—OH (via preactivation of Fmoc-Leu—OH to Fmoc-Leu—OSu) in 71.3% yield (estimated purity >95% by analytical HPLC). The tripeptide-resin was subjected to two cycles of solid phase synthesis with Fmoc-Tyr(tBu)—OH and Fmoc-Lys(Alloc)-OH, respectively. A portion of the resultant pentapeptide-resin was subjected to two more cycles of solid phase synthesis, in turn, with Fmoc-Lys(Boc)—OH and Fmoc-Ala—OH. An aliquot of the fully protected heptapeptide-resin was cleaved with 0.5% TFA-CH$_2$Cl$_2$ and gave 1 major peak (estimated purity >82%) by HPLC. Selective removal of the Lys(Alloc)[21]-protecting group was achieved with Pd[(C$_6$H$_5$)$_3$P]$_2$ and Bu$_3$SnH and the resultant partially protected heptapeptide-resin was cleaved with 0.5% TFA-CH$_2$Cl$_2$. A total of five 10-minute cleavages was required to completely cleave the resin. The product, Fmoc-Ala—Lys(Boc)—Lys—Tyr(tBu)—Leu—Asn—Asp(OBzl) was determined to be >80% pure by analytical HPLC and obtained in an overall yield of 75.7% (compared to the loading of the starting resin, Fmoc-Asp(O-Sasrin)-OBzl).

The side-chain to side-chain cyclization (Lys[21] to Asp[25]) of the linear heptapeptide was carried out in solution containing DMF using BOP and DIPEA and was complete in 1.25 hours. Analytical HPLC of this crude product revealed nearly complete conversion of the linear heptapeptide. A single purification step of the resultant cyclic heptapeptide was carried out on silica gel. This purification step removed any oligomers formed during the lactamization. Analytical HPLC of the purified product revealed that the cyclic heptapeptide was >98% pure. The overall yield of the purified cyclic heptapeptide compared to the starting resin was 37%.

Final deprotection of the C-terminal benzyl ester was achieved by hydrogenolysis in a vibromixer apparatus using 10% Pd on carbon over a period of about 6 hours. The reaction was followed by analytical HPLC and the final product, cyclo(Lys[21]—Asp[25])-Fmoc-Ala[19]—Lys(Boc)[20]—Lys[21] —Tyr(tBu)[22]—Leu[23]—Asn[24]—Asp[25]—OH was obtained in an overall yield of 33.7% (compared to the starting resin) with >97% purity. The structure and identity of the final product was confirmed by $^1$H-NMR spectroscopy and fully characterized by amino acid analysis and mass spectroscopy.

Repetitive solid phase synthesis of Fragment III, Fmoc-(9–18)-OH, described in Examples 16–26, and Fragment IV, Ac-(1–8)-OH, described in Examples 27–36), was carried out using BOP as the coupling reagent and piperidine for the deprotection of the Fmoc protecting group. Highly acid-labile Sasrin linker was used to retain side-chain protecting groups on the fragments. Generally, two coupling reactions were performed for each amino acid to ensure final purity. Two equivalents of reagent were used for the first coupling and one equivalent of reagent was used for the second or third coupling.

The average purity obtained after cleavage was 91% for peptide fragment III and 95% for peptide fragment IV. These peptide purities obtained after cleavage were satisfactory for direct use in the peptide fragment covergent synthesis of the VIP analog without further purification.

The synthesis of the novel cyclic VIP analog of the present invention was achieved by the coupling of the four fragments I–IV and is illustrated below.

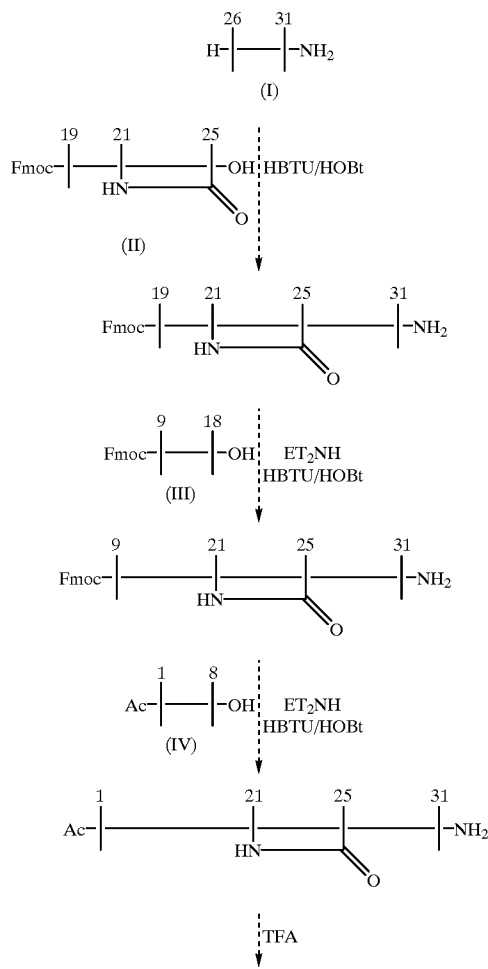

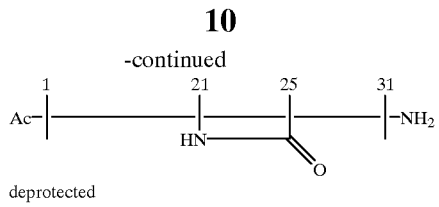

deprotected

Each cycle of fragment coupling was carried out by the same procedure as follows: (i) deprotection of the Fmoc-protecting group of one peptide fragment with 10% Et$_2$NH in DMF (2 hours); (ii) removal of fluorene by washing with hexane-ether; (iii) coupling of the deprotected peptide fragment with 1.0 equivalent of another protected fragment using HBTU (1.2 eq), HOBt (3.6 eq) in DMF-CH$_2$Cl$_2$ at 0°/30 minutes-1 h and 25°/3 h using DIPEA (4.8 eq); and (iv) evaporation and dissolution in CH$_2$Cl$_2$ and extraction with saturated NaHCO$_3$ and 10% citric acid.

In a preferred embodiment, each cycle of fragment coupling was carried out as follows: (i) deprotection of the Fmoc-protecting group of peptide Fragment I with 10% Et$_2$NH in DMF (2 hours); (ii) removal of fluorene by washing with hexane-ether; (iii) coupling of deprotected peptide Fragment I with 1.0 equivalent of protected peptide Fragment II using HBTU (1.2 eq), HOBt (3.6 eq) in DMF-CH$_2$Cl$_2$ at 0°/30 minutes-1 h and 25°/3 h using DIPEA (4.8 eq); and (iv) evaporation and dissolution in CH$_2$Cl$_2$ and extraction with saturated NaHCO$_3$ and 10% citric acid yielding protected intermediate Fmoc(19–31)-NH$_2$; (v) deprotection of the Fmoc-protecting group of intermediate Fmoc(19–31)-NH$_2$ with 10% Et$_2$NH in DMF (2 hours); (vi) removal of fluorene by washing with hexane-ether; (vii) coupling of deprotected intermediate Fmoc(19–31)-NH$_2$ with 1.0 equivalent of protected Fragment III using HBTU (1.2 eq), HOBt (3.6 eq) in DMF-CH$_2$Cl$_2$ at 0°/30 minutes-1 h and 25°/3 h using DIPEA (4.8 eq); and (viii) evaporation and dissolution in CH$_2$Cl$_2$ and extraction with saturated NaHCO$_3$ and 10% citric acid yielding protected intermediate Fmoc(9–31)-NH$_2$; (ix) deprotection of the Fmoc-protecting group of intermediate Fmoc(9–31)-NH$_2$ with 10% Et$_2$NH in DMF (2 hours); (x) removal of fluorene by washing with hexane-ether; (xi) coupling of deprotected intermediate Fmoc(9–31)-NH$_2$ with 1.0 equivalent of protected Fragment IV using HBTU (1.2 eq), HOBt (3.6 eq) in DMF-CH$_2$Cl$_2$ at 0°/30 minutes-1 h and 25°/3 h using DIPEA (4.8 eq); and (xii) evaporation and dissolution in CH$_2$Cl$_2$ and extraction with saturated NaHCO$_3$ and 10% citric acid yielding protected intermediate Ac-(1–31)-NH$_2$.

The fragment convergent synthesis of the cyclic VIP analog is described in detail in Examples 37 through 41. The protected intermediates, Fmoc(19–31)-NH$_2$, Fmoc(9–31)-NH$_2$, and Ac(1–31)-NH$_2$ were obtained as the major product from each reaction mixture cycle. These crude protected intermediates were not purified further and were used in their crude forms for each subsequent coupling cycle. Analytical HPLC confirmed that the starting materials were fully consumed under the conditions employed.

Final deprotection of the fully protected peptide Ac(1–31)-NH$_2$ was achieved by reaction with TFA (90%): EDT (3%); thioanisole (5%) and anisole (2%) at 25° for 2 hours. Analytical HPLC confirmed that the cyclic VIP analog was the major product (72–75%) of the synthesis.

Purification of the crude product was achieved in a single pass by preparative HPLC using a YMC ODS-A reverse phase column (4.7× 50 cm). Further scaling up to 4.0 g of crude product was readily achieved using this column and a total of 8.48 g of purified cyclic VIP analog, or 85.2% of the estimated total of 9.95 g (from HPLC analysis) of cyclic VIP analog present in the crude product, was isolated. This corresponds to an overall yield of the synthesis of 23.9%, which includes the coupling reactions, deprotection and purification steps. The cyclic VIP analog prepared by this method was shown to be homogeneous (>99%) by analytical HPLC and capillary zone electrophoresis. The identity of the cyclic VIP analog was confirmed by FAB mass spectroscopy and amino acid analysis.

EXAMPLES

Examples 1–8 describe the solid phase synthesis of protected Fragment I, Fmoc-(26–31-$NH_2$), Fmoc-Leu—Lys(Boc)—Lys(Boc)—Gly—Gly—Thr(t-Bu)—$NH_2$. Examples 9 through 15 describe the synthesis of Fragment II, cyclo($Lys^{21}$—$Asp^{25}$)-Fmoc-$Ala^{19}$—$Lys(Boc)^{20}$—$Lys^{21}$—$Tyr(tBu)^{22}$—$Leu^{23}$—$Asn^{24}$—$Asp^{25}$k—OH. Examples 16 to 26 describe the solid phase synthesis of protected Fragment III, Fmoc-(9–18)-OH, Fmoc-Asn—Tyr(tBu)—Thr(tBu)—Lys(Boc)—Leu—Arg(Pmc)—Lys(Boc)—Gln—Nle—Ala—OH. Examples 27 to 36 describe the solid phase synthesis of Protected Fragment IV, Ac—(1–8)—OH, Ac—His(Trt)—Ser(tBu)—Asp(OtBu)—Ala—Val—Phe—Thr(tBu)—Glu(OtBu)—OH. The synthesis of the cyclic VIP analog, Ac(1–31)—$NH_2$, is described in Examples 37 to 41.

Example 1

Preparation of (3)-XAL-Resin 150 g of benzhydrylamine (BHA) resin (loading: 0.54 meq/g, lot # 13933) was neutralized with 2×1500 ml of NMP containing 10% triethylamine, then washed with 1000 ml of DMF, 1000 ml of MeOH, 1000 ml of $CH_2Cl_2$, 1000 ml of MeOH and 3×1000 ml of $CH_2Cl2$. 96.3 g of (3)-XAL-linker (0.18 mol, 2.2 eq.), 79.6 g of BOP (0.18 mol) and 24.3 g of HOBt (0.18 mmol) were dissolved in 200 ml of NMP. 47.03 ml of DIPEA was added and the solution was added in one portion to a reactor containing the neutralized resin. The mixture was agitated for 90 minutes.

An aliquot was removed and washed with DMF and MeOH. Loading of the XAL-linker was determined by UV analysis to be 0.365 mmol/g. The XAL-resin was washed with 1000 ml of DMF, 1000 ml of MeOH, 1000 ml of $CH_2Cl_2$ and 2×1000 ml of MeOH. The uncoupled BHA resin was blocked with 1000 ml of 10% acetic anhydride and 10% DIPEA in $CH_2Cl_2$ for 30 minutes. The resin was then filtered and washed with 1000 ml of $CH_2Cl_2$, 1000 ml of MeOH, 2×1000 ml of $CH_2Cl_2$ and 2×1000 ml of MeOH.

Example 2

Preparation of Fmoc-Thr(t-Bu)-XAL-BHA Resin

For the first coupling, a mixture of 119.2 g of Fmoc-Thr(t-Bu)—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the XAL-resin prepared in Example 1. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling, a mixture of 59.6 g of Fmoc-Thr(t-Bu)—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

Example 3

Preparation of Fmoc-Gly—Thr(t-Bu)-XAL-BHA Resin

Deprotection of the Fmoc protecting group of Fmoc-Thr(t-Bu)-XAL-BHA was conducted according to the procedure described in Protocol 1. Coupling of Fmoc-Gly—OH to Thr—(t-Bu)-XAL-BHA was conducted as follows:

For the first coupling, a mixture of 89.2 g of Fmoc-Gly—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the Thr(t-Bu)-XAL-BHA resin. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling, a mixture of 44.6 g of Fmoc-Gly—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Gly—Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

Example 4

Preparation of Fmoc-Gly—Gly—Thr(t-Bu)-XAL-BHA Resin

Deprotection of the Fmoc protecting group of Fmoc-Gly—Thr(t-Bu)-XAL-BHA resin was conducted according to the procedure described in Protocol 1. Coupling of Fmoc-Gly—OH to Gly—Thr(t-Bu)-XAL-BHA resin was conducted as follows:

For the first coupling, a mixture of 89.2 g of Fmoc-Gly—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the Gly—Thr(t-Bu)-XAL-BHA resin. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling, a mixture of 44.6 g of Fmoc-Gly—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Gly—Gly—Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

Example 5

Preparation of Fmoc-Lys(Boc)—Gly—Gly—Thr(t-Bu)-XAL-BHA

Deprotection of the Fmoc protecting group of Fmoc-Gly—Gly—Thr(t-Bu)-XAL-BHA resin was conducted according to the procedure described in Protocol 1. Coupling of Fmoc-Lys—(Boc)—OH to Gly—Gly—Thr(t-Bu)-XAL-BHA resin was conducted as follows:

For the first coupling, a mixture of 140.5 g of Fmoc-Lys (Boc)—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the Gly—Gly—Thr(t-Bu)-XAL-BHA resin. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling a mixture of 70.3 g of Fmoc-Lys(Boc)—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Lys(Boc)—Gly—Gly—Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

Example 6

Preparation of Fmoc-Lys(Boc)—Lys(Boc)—Gly—Gly—Thr(t-Bu)-XAL-BHA

Deprotection of the Fmoc protecting group of Fmoc-Lys (Boc)—Gly—Gly—Thr(t-Bu)-XAL-BHA resin was conducted according to the procedure described in Protocol 1. Coupling of Fmoc-Lys—(Boc)—OH to Lys(Boc)—Gly—Gly—Thr(t-Bu)-XAL-BHA resin was conducted as follows:

For the first coupling, a mixture of 140.5 g of Fmoc-Lys (Boc)—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the Lys(Boc)—Gly—Gly—Thr(t-Bu)-XAL-BHA resin. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling a mixture of 0.3 g of Fmoc-Lys (Boc)—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Lys(Boc)—Lys(Boc)—Gly—Gly—Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

Example 7

Preparation of Fmoc-Leu—Lys(Boc)—Lys(Boc)—Gly—Gly—Thr(t-Bu)-XAL-BHA Resin

Deprotection of the Fmoc protecting group was of Fmoc-Lys(Boc)—Lys(Boc)—Gly—Gly—Thr(t-Bu)-XAL-BHA resin conducted according to the procedure described in Protocol 1. Coupling of Fmoc-Leu—OH to Lys(Boc)—Lys (Boc)—Gly—Gly—Thr(t-Bu)-XAL-BHA resin was conducted as follows:

For the first coupling, a mixture of 106 g of Fmoc-Leu—OH (300 mmol), 132 g of BOP (300 mmol) and 40.5 g of HOBt (300 mmol) was dissolved in 1000 ml of NMP with stirring at room temperature. 78.4 ml of DIPEA was added to the above solution, and the mixture was vigorously stirred. The resulting reagent was added in one portion to the Lys(Boc)—Lys(Boc)—Gly—Gly—Thr(t-Bu)-XAL-BHA resin. The mixture was agitated for 90 minutes.

After filtration, the resin was washed with 1000 ml of DMF (3 minutes), 1000 ml of MeOH (3 minutes), 1000 ml of $CH_2Cl_2$ (3 minutes) and 2×1000 ml of MeOH (3 minutes).

For the second coupling a mixture of 53 g of Fmoc-Leu—OH (150 mmol), 66.3 g of BOP (150 mmol) and 20.2 g of HOBt (150 mmol) were dissolved in 1000 ml of NMP with stirring at room temperature. 39.2 ml of DIPEA was added to the above solution, and the mixture was vigorously stirred. The resulting reagent was added in one portion to the resin, and the mixture was agitated for 90 minutes.

After filtration, the Fmoc-Leu—Lys(Boc)—Lys(Boc)—Gly—Gly—Thr(t-Bu)-XAL-BHA resin was washed with 1000 ml of DMF (3 minutes), 1000 ml of MeOH (3 minutes), 1000 ml of $CH_2Cl_2$ (3 minutes) and 2×1000 ml of MeOH (3 minutes).

The final weight of the peptide resin fragment Fmoc-Leu—Lys(Boc)—Lys(Boc)—Gly—Gly—Thr(t-Bu)-XAL-BHA resin, also known as Fmoc-(26–31)-XAL-BHA resin, was 267 g.

Example 8

Cleavage of the Fmoc-(26–31)-XAL-BHA Resin

In a 500 ml round bottom flask 10 g of the protected Fmoc-(26–31)-XAL-BHA was charged with 200 ml of 0.5% TFA in $CH_2Cl_2$. The slurry was stirred for 0.5 minutes at room temperature and then filtered. The filtrate was immediately adjusted to pH 7 by the addition of pyridine. The filtrate was evaporated at room temperature on a rotovac. The residue was triturated with 200 ml of distilled water then washed with 2×200 ml of ether. The resulting solid material was dried in vacuo to give the protected Fmoc-(26–31)-$NH_2$.

The filtered peptide-resin was then treated five more times with 200 ml of 0.5% TFA solution for 15 minutes, followed by adjusting the pH to 7 with pyridine. After evaporation, trituration and drying, a sample from each of the cleavages was analyzed by HPLC. The HPLC conditions were column: Lichrosorb RP-18, 5 m, 25 cm; eluants: (a) 0.1 M $HClO_4$/$H_2O$ (pH 2.5), (b) MeCN; gradient: 34% to 39% MeCN/20 minutes; flow rate: 1 ml/minute; and detector: 210 nm Knau.

All the peptide fragments above 90% purity were combined to give a total of 3.01 g. The purity of the combined material was 94.5%.

Example 9

Preparation of Fmoc-Asp(O-Sasrin Resin)-OBzl

2-Methoxy-4-alkoxybenzyl alcohol copolystyrene 1% divinylbenzene cross-linked resin (Sasrin-resin, 25 g, 0.96 meq/g, 24 meq.) was washed with DMF (2×500 ml) and $CH_2Cl_2$ (3×500 ml). Fmoc-Asp- -O-benzyl ester (35 g, 78.56 mmole, 3.27 eq.) in $CH_2Cl_2$ (400 ml) was added and shaken using a mechanical shaker. A solution of DCC (16.2 g, 78.5 mmole, 3.27 eq) in CH2Cl2 (100 ml) was added followed by the addition of N-methylmorpholine (3.36 ml, 30 mmole, 3.27 eq.) and 4-dimethylaminopyridine (0.293 g, 2.4 mmole, 0.1 eq.) and shaken for 5 hours. An aliquot was removed, washed with methanol and dried. The loading by UV analysis was determined to be 0.60 mmol/g-resin. The resin was washed wth DMF (2×500 ml) and methanol (5×500 ml) and dried in vacuo to give 32.8 g of Fmoc-Asp (O-Sasrin-Resin)-OBzl. A 10 g portion of this resin was suspended in DMF (180 ml) and a solution of benzoic anhydride (6.78 g. 30 mmol, 5 eq.) in DMF (40 ml) was added followed by DIPEA (5.22 ml, 30 mmole, 5 eq.) and the suspension shaken for 30 minutes. The resin was washed with DMF (5×200 ml) and the substitution was determined to be 0.60 mmol/g.

Example 10

Synthesis of $N^\alpha$-Fmoc-L-Leucyl-L-Asparagine (Fmoc-Leu—Asn—OH)

Fmoc-L-Leu—OH (10 g,28.32 mmol) was dissolved in a mixture of DMF (10 ml)-$CH_2Cl_2$ (70 ml) and cooled in an ice-bath. N-Hydroxysuccinimide (3.58 g, 31.14 mmol, 1.1 equiv.) and dicyclohexylcarbodiimiide (6.06 g, 31.14 mmol, 1.1 equiv.) were added and the mixture was stirred at 0° C. for 1 hour and 25° C. for 14 hour. The reaction mixture was cooled in an ice-bath, filtered and the precipitate washed with $CH_2Cl_2$ (40 ml). The filtrate was evaporated to dryness and the residue dissolved in a mixture of dioxane (80 ml)-$H_2O$ (10 ml) to form a solution of Fmoc-Leu-OSu. A solution of anhydrous L-asparagine (5.606 g, 42.48 mmol, 1.5 equiv.) in 60 ml of $Na_2CO_3$ (2.50 g, 42.28 mmol, 1.5 equiv.) was added to the above solution of Fmoc-Leu-OSu. An additional 10 ml of dioxane was added and the reaction mixture was stirred at 25° C. for 2 hours. Ethyl acetate (200 ml) was added to the reaction mixture and the pH adjusted to about 2 by the addition of 5% aqueous HCl with stirring. The EtOAc layer was separated and the aqueous layer was extracted 4 more times with 100 ml each. The combined EtOAc extract was washed with saturated NaCl (100 ml), $H_2O$ (3×100 ml), dried over anhydrous $Na_2SO_4$, filtered and evporated to dryness. The residue was dissolved in DMF (60 ml) with warming (40–45° C.) and $H_2O$ added to the cloud point. The product crystallized after standing overnight. It was filtered, washed with ether and recrystallized from DMF-$H_2O$. Lyophilization from dioxane gave 9.45 g (71.3%) of product. NMR and FAB mass spectroscopy confirmed the molecular formula $C_{25}H_{29}N_3O_6$ with an observed mass for $(M+H)^+$, 468.3. The product Fmoc-Leu—Asn—OH was shown to be >95% pure by analytical HPLC (FIG. 4). HPLC conditions were: column: Lichrosorb RP-8 (5$\mu$); eluant: (A) 0.1 M $NaClO_4$ (pH 2.5)-(B) $CH_3CN$; gradient: 40%–80% (B) in 20 minutes; flow 1 ml/minute.; and detection: 210 nm.

Example 11

Preparation of Fmoc-Ala—Lys(Boc)—Lys(Alloc)-Tyr (tBu)—Leu—Asn—Asp(O-Sasrin Resin)-OBzl Solid phase peptide synthesis was carried out as follows (20 ml of solvent/g of resin was used): 1) 20% piperidine/DMF, 1 minute; 2) 20% Piperidine.DMF, 10 minutes; 3) DMF, 4×2 minutes; 4) NMP, 1×2 minutes; 5) coupling of the protected amino acids as described herein; and 6) DMF, 3×2 minutes.

Solid phase peptide synthesis was carried out as described above starting with 10 g, 0.60 mmol/g. 6.0 mmol of Fmoc-Asp(O-Sasrin)-OBzl. Fmoc-Leu—Asn—Asp(O-Sasrin-resin)-OBzl was prepared by coupling the dipeptide, Fmoc-Leu—Asn—OH to H-Asp(O-Sasrin-resin)-OBzl as follows:

To Fmoc-Asn—Leu—OH, 4.2 g, 9 mmol, 1.5 eq. was added HBTU, 3.41 g, 9 mmol, 1.5 eq.; HOBT, 4.13 g, 27 mmol, 4.5 eq; DIPEA, 3.135 ml, 18 mmol, 3 eq; and NMP/$CH_2Cl_2$ (1:1) 220 ml. The mixture was coupled for 1.25 hours. For this particular coupling, Fmoc-Leu—Asn—OH was dissolved in 160 ml of NMP-$CH_2Cl_2$ (1:1). Since mixing of NMP and $CH_2Cl_2$ was exothermic the solvent was cooled prior to addition to the peptide and added to the H-Asp(O-Sasrin-resin)-OBzl followed by DIPEA and HOBt and the reaction vessel was shaken for 2 minutes. Then 30 ml of cold $CH_2Cl_2$ was added and finally a solution of HBTU dissolved in 20 ml of NMP-$CH_2Cl_2$ (1:1) and 10 ml of NMP was added. The ratio of NMP:CH2Cl2 was kept (1:1). The pH of the coupling reaction was maintained at 5–6.

Fmoc-Tyr(tBu)—Leu—Asn—Asp(O-Sasrin-resin)-OBzl was prepared by coupling Fmoc-Tyr(tBu)—OH to the resin as follows: to Fmoc-Tyr(tBu)—OH, 5.4 g, 12 mmol, 2 eq. was added HBTU, 3.4 g, 12 mmol, 2 eq; HOBt, 1.8 g, 12 mmol, 2 eq; DIPEA, 5.75 ml, 33 mmol, 5.5 eq; and NMP, 220 ml. This mixture was added to the resin and coupled for 1 hour.

Fmoc-Lys(Alloc)—Tyr(tBu)—Leu—Asn—Asp(O-Sasrin-resin)-OBzl was prepared by coupling Fmoc-Lys (Alloc)—OH to the resin as follows: to Fmoc-Lys(Alloc)—OH, 5.4 g, 12 mmol, 2 eq was added HBTU, 3.4 g, 12 mmol, 2 eq; HOBt, 1.8 g, 12 mmol, 2 eq; DIPEA, 5.75 ml, 33 mmol, 5.5 eq; and NMP, 220 ml. This mixture was added to the resin and coupled for 1 hour.

After the addition of Fmoc-Lys(Alloc)—OH, the resin was washed with methanol and dried to yield 13.3 g (0.45 mmol/g , 5.98 mmol) of the protected Fmoc-(21–25)-(O-Sasrin-resin)-OBzl. One-half of this peptide-resin (6.65 g, 2.99 mmol) was subjected to two additional cycles of solid phase synthesis as described above and coupled with Fmoc-Lys(Boc)—OH as follows: to Fmoc-Lys(Boc)—OH, 2.8 g, 6 mmol, 2 eq.was added BOP, 2.65 g, 6 mmol, 2 eq; HOBt, 0.918 g, 6 mmol, 2 eq; DIPEA, 3.25 ml, 18.65 mmol, 6.2 eq; and NMP 120 ml. This was added to the resin and coupled for 1 hour; and Fmoc-Ala—OH, as follows: to Fmoc-Ala—OH, 1.86 g, 6 mmol, 2 eq. was added HBTU, 2.27 g, 6 mmol, 2 eq; HOBt, 0.90 g, 6 mmol, 2 eq; and NMP 120 ml. The mixture was added to the resin and coupled for 1 hour.

The resin was washed with DMF (3×120 ml) and methanol (4×120 ml) and dried in vacuo to give 7.3 g (0.39 mmol/g, 2.84 mmole) of protected Fmoc (19–25)-(O-Sasrin-resin)-OBzl. A portion of Fmoc (19–25)-(O-Sasrin-resin)-OBzl was cleaved with 0.5% TFA-$CH_2Cl_2$ and evaluated by analytical HPLC to be >82% pure.

Example 12

Fmoc-Ala—Lys(Boc)—Lys—Tyr(tBu)—Leu—Asn—Asp (O-Sasrin Resin)-OBzl via deprotection of Fmoc-Ala—Lys (Boc)—Lys(Alloc)—Tyr(tBu)—Leu—Asn—Asp(O-Sasrin Resin)-OBzl The protected hexapeptide-resin Fmoc-Ala—Lys(Boc)—Lys(Alloc)—Tyr(tBu)—Leu—Asn—Asp(O-Sasrin)-OBzl (7.2 g, 0.39 mmol/g, 2.8 mmol) was suspended in 130 ml of $CH_2Cl_2$ and bubbled with helium. Acetic acid (0.330 ml, 5.75 mmol), bis(triphenyl phosphine) palladium dichloride (0.138 g,0.196 mmol) and tributyltin hydride (3.165 ml, 11.9 mmol) were added and the peptide-resin was bubbled with helium for 1.5 hours and the reaction vessel was drained. The above reaction was repeated a total of 5 times to ensure complete deprotection of the Alloc-group. An aliquot of peptide-resin was cleaved with 0.5% TFA/$CH_2Cl_2$ and analytical HPLC showed complete deprotection of the Alloc group. The resin was washed with $CH_2Cl_2$ (2×120 ml) and methanol (4×120 ml) and dried in vacuo to give 7.1 g (0.40 mmol/g, 2.84 mmole) of the partially protected peptide-resin Fmoc-Ala—Lys(Boc)—Lys—Tyr(tBu)—Leu—Asn—Asp (O-Sasrin)-OBzl.

Example 13

Cleavage of Fmoc-Ala—Lys(Boc)—Lys—Tyr(tBu)—Leu—Asn—Asp(O-Sasrin Resin)-OBzl: Preparation of Fmoc-Ala—Lys(Boc)Lys—Tyr(tBu)—Leu—Asn—Asp-OBzl 7.1 g (2.84 mmol) of the partially protected Fmoc-(19–25)-Sasrin-resin-OBzl was treated with 0.5% TFA in $CH_2Cl_2$ (140 ml) for 10 minutes at room temperature, filtered and the filtrate immediately adjusted to pH 6–7 with the addition of pyridine. The peptide-resin was subjected to four more treatments with 0.5% TFA in $CH_2Cl_2$ as described above and the filtrates were combined and evaporated. The peptide was triturated with water, filtered, washed liberally with water and dried in vacuo. The crude peptide was washed with anhydrous ether and dried in vacuo to give 3.26 g (overall yield, 75.7%) of the partially protected Fmoc-Ala—Lys(Boc)—Lys—Tyr(tBu)—Leu—Asn—Asp-OBzl which was determined to be >80% pure by analytical HPLC.

Example 14

Cyclization of Linear Heptapeptide: Preparation of Fmoc-Ala—Lys(Boc)—Lys—Tyr(tBu)—Leu—Asn—Asp-OBzl cyclo(lys21→Asp25)

A solution of the partially protected linear heptapeptide Fmoc-Ala—Lys(Boc)—Lys—Tyr(tBu)—Leu—Asn—Asp-OBzl 3.26 g (2.271 mmol) in 100 ml of DMF was added slowly over a period of 20 minutes to a magnetically stirred solution of BOP reagent 2.0 g (4.53 mmol, 2 eq.) and DIPEA 3.16 ml (18.14 mmol, 8 eq.) in 500 ml of DMF. After stirring at room temperature for 1.25 hours, an aliquot was removed and analytical HPLC indicated that the linear peptide was completely cyclized. The reaction mixture was stirred for an additional hour, acidified with acetic acid and evaporated to about 20 ml and distilled water (200 ml) was added. The precipitate was collected by filtration, washed thoroughly with distilled water and dried in vacuo. The product was washed with anhydrous ether and dried to give 3.0 g of the protected cyclic heptapeptide. Analytical HPLC showed nearly complete conversion of the linear peptide to the cyclic heptapeptide. This material was dissolved in 100 ml of 10% methanol in $CH_2Cl_2$. The insolubles (oligomers) were removed by filtering the solution through celite and the filtrate evaporated to give 2.85 g of crude protected cyclic peptide. This material was dissolved in 100 ml of $CH_2Cl_2$ and loaded onto a Waters Prep Pack Silica Gel Column (4.7×30 cm, 15–20 $\mu$); flow rate: 50 ml/minute; detection: 280 nm. The column was eluted in turn with $CH_2Cl_2$ (500 ml), 5% MeOH in $CH_2Cl_2$(2000 ml) and finally eluted with 8% MeOH in $CH_2Cl_2$. The fractions containing pure peptide (as determined by analytic HPLC) were pooled, evaporated to dryness and lyophilized from dioxane to give 1.445 g of purified cyclic heptapeptide (overall yield, 37%) which analytical HPLC revealed to be >98% pure.

Example 15

Preparation of Fmoc-Ala—Lys(Boc)—Lys-Tyr(tBu)—Leu—Asn—Asp—OH cyclo(lys21→Asp25)

The fully protected cyclic heptapeptide of Example 14 (1.445 g, 1.111 mmol) was dissolved in 60 ml of MeOH in a vibromixer flask under a stream of helium. To this was added 0.314 g of 10% Pd on carbon and the reaction mixture was hydrogenated for 3.5 hours in the vibromixer apparatus. Analytical HPLC indicated that about 30% of the benzyl ester fully protected cyclic heptapeptide remained. An additional 0.2 g of 10% Pd on carbon was added and hydrogenation was continued for 2.75 hours. Analytical HPLC indicated that complete deprotection of the benzyl group had occurred. The reaction mixture was filtered through celite and washed with MeOH. The filtrate and washings were evaporated and lyophilized from dioxane to give 1.225 g (91.1% yield; overall yield 33.7%) of cyclic heptapeptide acid. Analytical HPLC revealed that the product was >97% pure. The product identity was characterized and confirmed by amino acid analysis, FAB-MS, optical rotation and $^1$H-NMR spectroscopy.

Example 16

Preparation of Fmoc-Ala-Sasrin Resin 50 g of 2-Methoxy-4-alkoxybenzyl alcohol copolystyrene 1% divinylbenzene cross-linked resin (Sasrin resin) was washed with 500 ml of methylene chloride, and 2×500 ml of DMF.

74.6 g of Fmoc-Ala—OH (240 mmol) was dissolved in 650 ml of $CH_2Cl_2$/DMF (2:1 volume ratio). The solution was cooled in an ice bath and 49.5 g of DCC (240 mmol) was added, followed by the addition of 1.46 g of 4-dimethylamino pyridine (12 mmol) and 6.27 ml of N-methylmorpholine (60 mmol). The mixture was agitated on an orbital rotary shaker for 9 hours.

The resin was filtered and washed with 500 ml of DMF (3 minutes), 500 ml of MeOH (3 minutes), 500 ml of $CH_2Cl_2$ (3 minutes) and 500 ml of MeOH (3 minutes).

An aliquot was removed, dried and the loading was determined by UV qualitative analysis to be 0.54 mmol/g.

The resin was then washed with 2×500 ml of $CH_2Cl_2$ (3 minutes) and 500 ml of DMF (3 minutes). The resin was then suspended in 400 ml of DMF, and 54.3 g of benzoic anhydride (240 mmol) was added, followed by the addition of 100 ml of DMF, and 41.7 ml of diisopropylethylamine (240 mmol). The suspension was shaken for 30 minutes. The resin was filtered and washed with 500 ml of $CH_2Cl_2$ (3 minutes), 500 ml of MeOH (3 minutes) 2×500 ml of $CH_2Cl_2$ (3 minutes), 500 ml of DMF (3 minutes) and 2×500 ml of MeOH (3 minutes).

Example 17

Preparation of Fmoc-Nle—Ala-Sasrin Resin

Deprotection of the Fmoc group of Fmoc-Ala-Sasrin Resin was conducted according to the procedure described in Protocol 1. The coupling of Fmoc-Nle—OH to Ala-Sasrin was conducted as follows:

For the first coupling a mixture of 19.08 g of Fmoc-Nle—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Ala-Sasrin resin, and the mixture was agitated for 2 hours.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 9.54 g of Fmoc-Nle—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Nle—Ala-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

Example 18

Preparation of Fmoc-Gln—Nle—Ala-Sasrin Resin

Deprotection of the Fmoc group of Fmoc-Nle—Ala-Sasrin was conducted according to the procedure described in Protocol 1.

For the first coupling a mixture of 19.9 g of Fmoc-Gln—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Nle—Ala-Sasrin resin, and the mixture was agitated for 2 hours.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 9.9 g of Fmoc-Gln—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Gln—Nle—Ala-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

Example 19

Preparation of Fmoc-Lys(Boc)—Gln—Nle—Ala-Sasrin Resin

Deprotection of the Fmoc group of Fmoc-Gln—Nle—Ala-Sasrin resin was conducted according to the procedure described in Protocol 1.

For the first coupling a mixture of 25.3 g of Fmoc-Lys(Boc)—Gln—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Gln—Nle—Ala-Sasrin resin, and the mixture was agitated for 2 hours.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 12.7 g of Fmoc-Lys(Boc)—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Lys(Boc)—Gln—Nle—Ala-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

Example 20

Preparation of Fmoc-Arg(Pmc)—Lys(Boc)—Gln—Nle—Ala-Sasrin Resin

Deprotection of the Fmoc group of Fmoc-Lys(Boc)—Gln—Nle—Ala-Sasrin was conducted according to the procedure described in Protocol 1.

For the first coupling a mixture of 40.1 g of Fmoc-Arg(Pmc)—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Lys(Boc)—Gln—Nle—Ala-Sasrin resin, and the mixture was agitated for 2 hours.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 20.1 g of Fmoc-Arg(Pmc)—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Arg(Pmc)—Lys(Boc)—Gln—Nle—Ala-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

Example 21

Preparation of Fmoc-Leu—Arg(Pmc)—Lys(Boc)—Gln—Nle—Ala-Sasrin Resin

Deprotection of the Fmoc group of Fmoc-Arg(Pmc)—Lys(Boc)—Gln—Nle—Ala-Sasrin was conducted according to the procedure described in Protocol 1.

For the first coupling a mixture of 19.1 g of Fmoc-Leu—OH (54 mmol), 23.9 of BOP (54 mmol) and 7.3 g of HOBt (54 mmol) was dissolved in 400 ml of NMP with stirring it room temperature. 14.1 ml of DIPEA was added to the above solution, and the mixture was vigorously stirred. The resulting reagent was added in one portion to the Arg(Pmc)—Lys(Boc)—Gln—Nle—Ala-Sasrin resin, and the mixture was agitated for 2 hours.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 9.6 g of Fmoc-Leu—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Leu—Arg(Pmc)—Lys(Boc)—Gln—Nle—Ala-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 22

Preparation of Fmoc-Lys(Boc)—Leu—Arg(Pmc)—Lys(Boc)—Gln—Nle—Ala-Sasrin Resin

Deprotection of the Fmoc group of Fmoc-Leu Arg(Pmc)—Lys(Boc)—Gln—Nle—Ala-Sasrin was conducted according to the procedure described in Protocol 1.

For the first coupling a mixture of 25.4 g of Fmoc-Lys(Boc)—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Leu—Arg(Pmc)—Lys(Boc)—Gln—Nle—Ala-Sasrin resin, and the mixture was agitated for 2 hours.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 12.7 g of Fmoc-Lys(Boc)—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Lys(Boc)—Leu—Arg(Pmc)—Lys(Boc)—Gln—Nle—Ala-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 23
Preparation of Fmoc-Thr(tBu)—Lys(Boc)—Leu—Arg(Pmc)—Lys(Boc)Gln—Nle—Ala-Sasrin Resin Deprotection of the Fmoc group of Fmoc-Lys(Boc)—Leu—Arg(Pmc)—Lys(Boc)—Gln—Nle—Ala-Sasrin was conducted according to the procedure described in Protocol 1.

For the first coupling a mixture of 28.7 g of Fmoc-Thr(tBu)—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Lys(Boc)—Leu—Arg(Pmc)—Lys(Boc)—Gln—Nle—Ala-Sasrin resin, and the mixture was agitated for 2 hours.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 14.4 g of Fmoc-Thr(tBu)—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc-Thr(tBu)—Lys(Boc)—Leu—Arg(Pmc)—Lys(Boc)Gln—Nle—Ala-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 24
Preparation of Fmoc-Tyr(tBu)—Thr(tBu)—Lys(Boc)—Leu—Arg(Pmc)—Lys(Boc)—Gln—Nle—Ala-Sasrin Resin Deprotection of the Fmoc group of Fmoc-Thr(tBu)—Lys(Boc)—Leu—Arg(Pmc)—Lys(Boc)—Gln—Nle—Ala-Sasrin resin was conducted according to the procedure described in Protocol 1.

For the first coupling a mixture of 24.8 g of Fmoc-Tyr(tBu)—OH (54 mmol), 23.9 of BOP (54 mmol) and 7.3 g of HOBt (54 mmol) was dissolved in 400 ml of NMP with stirring at room temperature. 14.1 ml of DIPEA was added to the above solution, and the mixture was vigorously stirred. The resulting reagent was added in one portion to the Thr(tBu)—Lys(Boc)—Leu—Arg(Pmc)—Lys(Boc)—Gln—Nle—Ala-Sasrin resin, and the mixture was agitated for 2 hours.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 12.4 g of Fmoc-Tyr(tBu)—OH (27 mmol), 11.9 g of BOP (27 mmol) and 3.65 g of HOBt (27 mmol) was dissolved in 400 ml of NMP and stirred at room temperature. 7.05 ml of DIPEA was added to the above solution, and the mixture was vigorously stirred. The resulting reagent was added in one portion to the resin and the mixture was agitated for 2 hours.

After filtration, the Fmoc group of Fmoc-Tyr(tBu)—Thr(tBu)—Lys(Boc)—Leu—Arg(Pmc)—Lys(Boc)—Gln—Nle—Ala-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 25
Preparation of Fmoc-Asn—Tyr(tBu)—0Thr(tBu)—Lys(Boc)—Leu—Arg(Pmc)—Lys(Boc)—Gln—Nle—Ala-Sasrin Resin Deprotection of the Fmoc group of Fmoc-Tyr(tBu)—Thr(tBu)—Lys(Boc)—Leu—Arg(Pmc)—Lys(Boc)—Gln—Nle—Ala-Sasrin was conducted according to the procedure described in Protocol 1 before the coupling of Fmoc-Asn—OH via a symmetric anhydride method.

19.4 g Fmoc-Asn—OH (54 mmol), and 7.3 g of HOBt (54 mmol) were dissolved in a mixture of 135 ml of CH$_2$Cl$_2$ and 270 ml of DMF. The mixture was stirred in an ice bath before 11.2 g of DCC (54 mmol) was added. The mixture was stirred for 30 minutes, was filtered and the filtrate was added in one portion to the Tyr(tBu)— Thr(tBu)—Lys(Boc)—Leu—Arg(Pmc)—Lys(Boc)—Gln—Nle—Ala-Sasrin resin (the (10–18) Sasrin resin). The coupling was completed in 90 minutes.

The resulting resin was then washed with 500 ml of DMF (3 minutes), 500 ml of MeOH (3 minutes), 500 ml of CH$_2$Cl$_2$ (3 minutes) and 2×500 mlof MeOH (3 minutes).

For the second coupling, 19.4 g Fmoc-Asn—OH (54 mmol), and 7.3 g of HOBt (54 mmol) were dissolved in a mixture of 135 ml of CH$_2$Cl$_2$ and 270 ml of DMF. The mixture was stirred in an ice bath before 11.2 g of DCC (54 mmol) was added. The mixture was stirred for 30 minutes, was filtered and the filtrate was added in one portion to the (10–18)-Sasrin resin. The coupling was completed in 90 minutes.

The resin was then washed with 500 ml of DMF (3 minutes), 500 ml of MeOH (3 minutes), 500 ml of CH$_2$Cl$_2$ (3 minutes) and 2×500 ml of MeOH (3 minutes). No deprotection was performed after the coupling was completed. The final weight of the product, Fmoc-Asn—Tyr(tBu)—Thr(tBu)—Lys(Boc)—Leu—Arg(Pmc)—Lys(Boc)—Gln—Nle—Ala-Sasrin resin (Fmoc(9–18)-Sasrin resin), was 112 g.

Example 26

Cleavage of Fmoc(9–18) from the Fmoc(9–18)-Sasrin resin 20 g of the Fmoc(9–18)-Sasrin resin was treated with 400 ml of 0.2% TFA in $CH_2Cl_2$ for 1 minute at room temperature, then filtered. The pH of the filtrate was immediately adjusted to pH 7 by the addition of pyridine. The filtrate was evaporated, and the residue was triturated with 50 ml of distilled water, then washed with 50 ml of ether. The resulting solid material was dried in vacuo.

The filtered peptide-resin was then treated six more times with 400 ml of 0.2% TFA solution for 10 minutes followed by adjustment of the pH to 7 with pyridine. After evaporation, trituration and drying the HPLC analysis was conducted. The conditions for analytical HPLC were: column: Lichrosorb RP-18, 5 M, 25 cm; eluants: (a) 0.1 M $HClO_4/H_2O$ (pH 2.5),(b) MeCN; gradient: 34% to 39% MeCN/20 minutes; flow rate: 1 ml/minute; and detector: 210 nm. All the peptide fragments above 90% purity were combined to give a total of 9.9 g. The 52 g of product obtained from the cleavage of 112 g of peptide resin had an average purity of 91%.

Example 27

Preparation of Fmoc-Glu(OtBu)-Sasrin Resin 50 g of 2-methoxy-4-alkoxybenzyl alcohol copolystyrene 1% divinylbenzene cross-linked resin (Sasrin resin) was washed with 500 ml of methylene chloride, and 2×500 ml of DMF.

102 g of Fmoc-Glu(OtBu)—OH (240 mmol) was dissolved in 500 ml of $CH_2Cl_2$/DMF (9:1 volume ratio). The solution was cooled in an ice bath, then a DCC solution, which was prepared by dissolving 49.5 g of DCC (240 mmol) in 100 ml of $CH_2Cl_2$/DMF (9:1), was added. The mixture was stirred for 30 minutes, then filtered to remove DCU. The filtrate was added to the above washed Sasrin resin, followed by the addition of 1.46 g of 4-dimethylaminopyridine (12 mmol) and 6.27 ml of N-methylmorpholine (60 mmol). The mixture was agitated on an orbital rotary for 9 hours.

The resin was filtered and washed with 500 ml of DMF (3 minutes), 500 ml of MeOH (3 minutes), 500 ml of $CH_2Cl_2$ (3 minutes) and 500 ml of MeOH (3 minutes). An aliquot was removed, dried and the loading was determined by UV analysis to be 0.59 mmol/g.

The resin was washed with 2×500 ml of $CH_2Cl_2$ (3 minutes) and 500 ml of DMF (3 minutes). The resin was then suspended in 400 ml of DMF, and 54.3 g of benzoic anhydride (240 mmol) was added, followed by the addition of 100 ml of DMF, and 41.7 ml of diisopropylethylamine (240 mmol). The suspension was shaken for 30 minutes. The Fmoc-Glu(OtBu)-Sasrin resin was filtered and washed with 500 ml of $CH_2Cl_2$ (3 minutes), 500 ml of MeOH (3 minutes), 2×500 ml of $CH_2Cl_2$ (3 minutes), 500 ml of DMF (3 minutes) and 2×500 ml of MeOH (3 minutes).

Example 28

Preparation of Fmoc-Thr(tBu)—Glu(OtBu)-Sasrin Resin

Deprotection of the Fmoc group of Fmoc-Glu—(OtBu)-Sasrin resin was conducted according to the procedure described in Protocol 1.

For the first coupling, a mixture of 23.4 g of Fmoc-Thr(tBu)—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Glu(OtBu)-Sasrin resin, and the mixture was agitated for 90 minutes.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 11.7 g of Fmoc-Thr(tBu)—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-Thr(tBu)—Glu(OtBu)-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

Example 29

Preparation of Fmoc-Phe—Thr(tBu)—Glu(OtBu)-Sasrin Resin

Deprotection of the Fmoc group of Fmoc-Thr(tBu)—Glu(OtBu)-Sasrin resin was conducted according to the procedure described in Protocol 1.

For the first coupling, a mixture of 22.8 g of Fmoc-Phe—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Thr(tBu)—Glu(OtBu)-Sasrin resin, and the mixture was agitated for 90 minutes.

After filtration, the Fmoc-Phe—Thr(tBu)—Glu(OtBu)-Sasrin resin was washed with 500 ml of DMF (3 minutes), 500 ml of MeOH (3 minutes), 500 ml of $CH_2Cl_2$ (3 minutes) and 2×500 ml of MeOH (3 minutes).

The ninhydrin test indicated that the coupling reaction was complete, therefore a second coupling was unnecessary.

Example 30

Preparation of Fmoc-Val—Phe—Thr(tBu)—Glu(OtBu)-Sasrin Resin

Deprotection of the Fmoc group of Fmoc-Phe—Thr(tBu)—Glu(OtBu)-Sasrin resin was conducted according to the procedure described in Protocol 1.

For the first coupling, a mixture of 20 g of Fmoc-Val—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Phe—Thr(tBu)—Glu(OtBu)-Sasrin resin, and the mixture was agitated for 90 minutes.

After filtration, the resin was washed with 500 ml of DMF (3 minutes), 500 ml of MeOH (3 minutes), 500 ml of $CH_2Cl_2$ (3 minutes) and 2×500 ml of MeOH (3 minutes).

For the second coupling, a mixture of 10 g of Fmoc-Val—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-Val—Phe—Thr(tBu)—Glu(OtBu)-Sasrin resin was washed with 500 ml of DMF (3 minutes), 500 ml of MeOH (3 minutes), 500 ml of CH$_2$Cl$_2$ (3 minutes) ind 2×500 ml of MeOH (3 minutes).

Example 31

Preparation of Fmoc-Ala—Val—Phe—Thr(tBu)—Glu(OtBu)-Sasrin Resin

Deprotection of the Fmoc group of Fmoc-Val—Phe—Thr(tBu)—Glu(OtBu)-Sasrin resin was conducted according to the procedure described in Protocol 1.

For the first coupling, a mixture of 18.4 g of Fmoc-Ala—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Val—Phe—Thr(tBu)—Glu(OtBu)-Sasrin resin, and the mixture was agitated for 90 minutes.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 9.2 g of Fmoc-Ala—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-Ala—Val—Phe—Thr(tBu)—Glu(OtBu)-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 32

Preparation of Fmoc-Asp(OtBu)—Ala—Val—Phe—Thr(tBu)—Glu(OtBu)-Sasrin Resin

Deprotection of the Fmoc group of Fmoc-Ala—Val—Phe—Thr(tBu)—Glu(OtBu)-Sasrin resin was conducted according to the procedure described in Protocol 1.

For the first coupling, a mixture of 24.3 g of Fmoc-Asp(OtBu)—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Ala—Val—Phe—Thr(tBu)—Glu(OtBu)-Sasrin resin, and the mixture was agitated for 90 minutes.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 12.1 g of Fmoc-Asp(OtBu)—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-Asp(OtBu)—Ala—Val—Phe—Thr(tBu)—Glu(OtBu)-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 33

Preparation of Fmoc-Ser(tBu)—Asp(OtBu)—Ala—Val—Phe—Thr(tBu)—Glu(OtBu)-Sasrin Resin Deprotection of the Fmoc group of Fmoc-Asp(OtBu)—Ala—Val—Phe—Thr(tBu)—Glu(OtBu)-Sasrin Resin was conducted according to the procedure described in Protocol 1.

For the first coupling, a mixture of 22.6 g of Fmoc-Ser(tBu)—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Asp(OtBu)—Ala—Val—Phe—Thr—(tBu)—Glu(OtBu)-Sasrin resin, and the mixture was agitated for 90 minutes.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 11.3 g of Fmoc-Ser(tBu)—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-Ser(tBu)—Asp(OtBu)—Ala—Val—Phe—Thr(tBu)—Glu(OtBu)-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 34

Preparation of Fmoc-His(Trt)—Ser(tBu)—Asp(OtBu)—Ala—Val—Phe—Thr(tBu)—Glu(OtBu)-Sasrin Resin Deprotection of the Fmoc group of Fmnoc-Ser(tBu)—Asp(OtBu)—Ala—Val—Phe—Thr(tBu)—Glu(OtBu)-Sasrin resin was conducted according to the procedure described in Protocol 1.

For the first coupling, a mixture of 36.6 g of Fmoc-His(Trt)—OH (59 mmol), 26.1 g of BOP (59 mmol) and 8.0 g of HOBt (59 mmol) was dissolved in 400 ml of NMP with stirring at room temperature. 15.4 ml of DIPEA was added to the above solution, and the mixture was vigorously stirred. The resulting reagent was added in one portion to the Ser(tBu)—Asp(OtBu)—Ala—Val—Phe—Thr(tBu)—Glu(OtBu)-Sasrin resin, and the mixture was agitated for 90 minutes.

After filtration, the resin was washed with 500 ml of DMF (3 minutes), 500 ml of MeOH (3 minutes), 500 ml of CH$_2$Cl$_2$ (3 minutes) and 2×500 ml of MeOH (3 minutes).

For the second coupling, a mixture of 18.3 g of Fmoc-His(Trt)—OH (29.5 mmol), 13.1 g of BOP (29.5 mmol) and 4.0 g of HOBt (29.5 mmol) was dissolved in 400 ml of NMP with stirring at room temperature. 7.7 ml of DIPEA was added to the above solution, and the mixture was vigorously stirred. The resulting reagent was added in one portion to the resin, and the mixture was agitated for 90 minutes.

After filtration, the Fmoc-His(Trt)—Ser(tBu)—Asp(OtBu)—Ala—Val—Phe—Thr(tBu)—Glu(OtBu)-Sasrin resin was washed with 500 ml of DMF (3 minutes), 500 ml of MeOH (3 minutes), 500 ml of CH$_2$Cl$_2$ (3 minutes) and 2×500 ml of MeOH (3 minutes).

Example 35
Acetylation of His(Trt)—Ser(tBu)—Asp(OtBu)—Ala—Val—Phe—Thr(tBu)—Glu(OtBu)-Sasrin Resin The protected peptide resin Fmoc-His(Trt)—Ser(tBu)—Asp(OtBu)—Ala—Val—Phe—Thr(tBu)—Glu(OtBu)-Sasrin resin was treated with 2×25% piperidine and washed as described for the deprotection step in Protocol 1. After the deprotection of the Fmoc group, acetylation of the N-terminus amine was conducted as follows:

A solution of 100 ml of Ac$_2$O and 100 ml of DIPEA in 800 ml of CH$_2$Cl$_2$ was added to the peptide resin and the reaction allowed to proceed for 90 minutes.

The resin was filtered, then washed successively with 500 ml of DMF (3 minutes), 500 ml of MeOH (3 minutes), 500 ml of CH$_2$Cl$_2$ (3 minutes) and 2×500 ml of MeOH (3 minutes), and dried in vacuo and gave 110 g of protected Ac(1–8)-Sasrin resin, Ac—His(Trt)—Ser(tBu)—Asp(OtBu)—Ala—Val—Phe—Thr(tBu)—Glu(OtBu)-Sasrin resin.

Example 36
Cleavage of Ac—His(Trt)—Ser(tBu)—Asp(OtBu)—Ala—Val—Phe—Thr(tBu)—Glu(OtBu)-Sasrin Resin 20 g of the protected Ac(1–8) Sasrin resin was treated with 400 ml of 0.5% TFA in CH$_2$Cl$_2$ for 1 minutes at room temperature, then filtered. The pH of the filtrate was immediately adjusted to pH 7 by the addition of pyridine. The filtrate was evaporated, and the residue was triturated with 50 ml of distilled water, then washed with 50 ml of ether. The resulting solid material was dried in vacuo. The filtered peptide-resin was then treated three more times with 400 ml of 0.5% TFA solution for 10 minutes, followed by adjusting the pH to 7 with pyridine. After evaporation, trituration and drying an HPLC analysis was conducted.

The filtered peptide-resin was treated three more times again with 400 ml of 0.3% TFA solution for 10 minutes, followed by adjusting the pH to 7 with pyridine. After evaporation, trituration and drying, HPLC analysis of the peptide fragment was conducted. The analytical HPLC conditions were: column: Lichrosorb RP-18, 5 μ, 25 cm; eluants: (a) 0.1 M HClO$_4$/H$_2$O (pH 2.5), (b) MeCN; gradient: 34% to 39% MeCN/20 minutes; flow rate: 1 ml/minute; and detector: 210 nm.

All the peptide fragments above 90% purity were combined to give a total of 10.8 g. The overall yield obtained from the cleavage of 110 g of peptide resin was 46 g, had an average purity of 95%.

Example 37
Synthesis of Fmoc-Ala—Lys(Boc)—Lys—Tyr(tBu)—Leu—Asn—Asp—Leu—Lys(Boc)—Lys(Boc)—Gly—Gly—Thr(tBu)—NH$_2$ (Protected Fmoc(19–31-NH$_2$)

Fragment I, Fmoc(26–31)-NH$_2$ (SEQ ID NO:2) (8.91 g, 8.24 mmol) was dissolved in 90 ml of 10% diethylamine in DMF and stirred at room temperature for 2 hours. The amine and the solvent were evaporated in vacuo and the residue was triturated with a mixture of hexane and ether (4:1), the solid product collected on a filter and washed with a mixture of hexane and ether (4:1), providing 7.0 g of H-(26–31)-NH$_2$ as a colorless powder (yield 98.9%).

Fragment II, Fmoc(19–25)-OH (SEQ ID NO: 3) (9.89 g, 8.15 mmol), H-(26–31)-NH$_2$ (7.0 g, 8.15 mmol), HOBt (4.49 g, 29.3 mmol) and DIPEA (6.81 ml, 39.1 mmol) were dissolved in 120 ml of DMF/CH$_2$Cl$_2$ (1:1), then stirred in an ice-water bath. Solid HBTU (3.71 g, 9.78 mmol) was added portionwise over a 10-minute period to the above solution. Stirring was continued at 0° for 30 minutes and then at room temperature for 3 hours. The solution was evaporated in vacuo to remove the solvents and the residue was dissolved in CH$_2$Cl$_2$. This solution was washed in turn with saturated NaHCO$_3$ (3 times), 10% aqueous citric acid (2 times), water and brine, and dried over anhydrous MgSO$_4$. The solution was filtered and the filtrate was evaporated providing crude protected intermediate Fmoc (19–31)-NH$_2$ as a colorless solid, 17.4 g (yield 100%). Purity was estimated to be about 70% by analytical HPLC.

Example 38
Synthesis of Fmoc-Asn—Tyr(tBu)—Thr(tBu)—Lys(Boc)—Leu—Arg—(Pmc)—Lys(Boc)—Gln—Nle—Ala—Ala—Lys(Boc)—Lys—Tyr(tBu)—Leu—Asn—Asp—Leu—Lys(Boc)—Lys(Boc)—Gly—Gly—Thr(tBu)—NH$_2$: (Protected Fmoc(9–31-NH$_2$)

Fmoc(19–31)-NH$_2$ (17.4 g) was dissolved in 90 ml of 10% diethylamine in DMF and stirred at room temperature for 2 hours. The amine and the solvent were removed in vacuo, and the residue was triturated with a mixture of hexane and ether (3:1), the solid collected on a filter and washed with a mixture of hexane and ether (3:1), providing 16.67 g of H-(19–31)-NH$_2$ as colorless solid (yield 100%).

Fmoc (9–18)-OH (SEQ ID NO:4) (16.59g, 8.15 mmol), H-(19–31)-NH$_2$ (16.67 g), HOBt (4.49 g, 29.3 mmol) and DIPEA (6.81 ml, 39.1 mmol) were dissolved in 150 ml of DMF/CH$_2$Cl$_2$ (2:1), (the solution was slightly cloudy), then stirred in an ice-water bath. HBTU (3.70 g, 9.78 mmol) was added portionwise to the above solution over a 10-minute period. The solution became clear and stirring was continued at 0° for 30 minutes, and then at room temperature for 3 hours. The solution was evaporated in vacuo to remove the solvents and the residue was dissolved in CH$_2$Cl$_2$. This solution was washed in turn with saturated NaHCO$_3$ (3 times), 10% aqueous citric acid (2 times), water and brine and dried over anhydrous MgSO$_4$. The solution was filtered and the filtrate was evaporated in vacuo to provide 24.77 g crude protected intermediate Fmoc (9–31)-NH$_2$ as colorless solid for a yield of about 79%. The product was determined to be about 69% pure by analytical HPLC.

Example 39
Synthesis of Ac—His(Trt)—Ser(tBu)—Asp(OtBu)—Ala—Val—Phe—Thr(tBu)—Glu(OtBu)—Asn—Tyr(tBu)—Thr(tBu)—Thr(tBu)—Lys(Boc)—Leu—Arg(Pmc)—Lys(Boc)—Gln—Nle—Ala—Ala—Lys(Boc)—Lys—Tyr(tBu)—Leu—Asn—Asp—Leu——Lys(Boc)—Lys(Boc)—Gly—Gly—Thr(tBu)—NH$_2$ (Protected Ac(1–31)-NH$_2$)

Fmoc(9–31)-NH$_2$ (24.77 g) was dissolved in 100 ml of 10% diethylamine in DMF and stirred at room temperature for 2 hours. The amine and the solvent were removed in vacuo, and the residue was triturated with a mixture of hexane and ether (3:1), the solid collected on a filter and washed with a mixture of hexane and ether (3:1), providing 22.56 g of H-(9–31)-NH$_2$ as colorless solid (yield 96.7%).

A solution of H-(9–31)-NH$_2$ (22.56 g 6.22 mmol), Ac(1–8)-OH (SEQ ID NO:5) (8.79 g, 6.22 mmol), HOBt (3.43 g, 22.38 mmol), and DIPEA (5.19 ml, 29.84 mmol) in 200 ml of DMF/CH$_2$Cl$_2$ (1:1), was stirred in an ice-water bath while HBTU (2.83 g, 7.46 mmol) was added portionwise to the above solution over a 10-minute period. The solution was stirred at 0° for 30 minutes and then at room temperature for 3 hours. The solution was evaporated and the residue was dissolved in CH$_2$Cl$_2$. This solution was washed in turn with saturated NaHCO$_3$ (3 times), 10% aqueous citric acid (2 times), water and brine, and dried over anhydrous MgSO$_4$. The solution was filtered and the filtrate was evaporated providing crude protected Ac(1–31)-NH$_2$ as a colorless solid, 29.54 g (yield 72.2%). Purity was estimated to be 78% by analytical HPLC.

Example 40

Deprotection of Protected Ac(1–31l)-NH2: Synthesis of the cyclic VIP Analog

Protected Ac(1–31)-NH$_2$ (29.54 g) was dissolved in 150 ml of a mixture of TFA (135 ml), EDT (4.5 ml), thioanisole (7.5 ml), anisole (3 ml) and stirred at room temperature for 2 hours. This solution was evaporated to remove TFA and poured into 500 ml of pre-cooled ether to give a precipitate which was collected and washed thoroughly with ether. The product was dried in vacuo to provide 25.5 g of Ac(1–31)-NH$_2$ as a colorless powder having a purity of about 72–75% as estimated by HPLC.

Example 41

Purification of the cyclic VIP Analog

Purification of the crude peptide Ac(1–31)-NH$_2$ was performed in multiple runs by preparative HPLC on a Delta Prep 3000 system. Quantitative HPLC analysis of an aliquot of the crude product of the Zorbax Protection Plus column (vs a standard of the cyclic VIP analog) revealed that 9.95 g of the analog was present in the crude product which weighed 25.5 g. For a typical run, the peptide (4 g) was dissolved in 200 ml of 0.1% TFA/H$_2$O and applied to a YMC ODS-A (120Å, 15 $\mu$) column (4.7×50 cm). The mobile phase was (A) 0.1% TFA/H$_2$O-(B) 0.1% TFA/50% MeOH—CH$_3$CN. A gradient elution was run starting at 20% (B) (10 minutes) and then 20%–50% (B) in 180 minutes at a flow rate of 80 ml/minute. UV detection was performed at 215 nm. Fractions containing the main peak were collected and evaluated by analytical HPLC. Fractions judged to be of high purity were pooled, concentrated on a cold finger rotary evaporator, and lyophilized to yield 1.2 g of the cyclic VIP analog Ac(1–31)-NH$_2$. The balance of the crude product was processed by the same method to give a total of 8.48 g (85.2% recovery) of purified cyclic VIP analog; overall yield 23.9%. Analytical HPLC and capillary electrophoresis confirmed that the product was >99% pure. The product was characterized and identity confirmed by amino acid analysis, FAB-MS, optical rotation, ultraviolet absorbance and circular dichroism.

---

What is claimed is:

1. A method for the synthesis of a compound Ac-(1–31)-NH$_2$ (SEQ ID NO:1) by coupling four Fmoc protected peptide fragments, peptide Fragment I (SEQ ID NO:2), peptide Fragment II (SEQ ID NO:3), peptide Fragment III (SEQ ID NO: IV) and peptide Fragment IV (SEQ ID NO:5), said method comprising:
   (a) deprotecting the Fmoc-protecting group of peptide Fragment I and coupling the deprotected peptide Fragment I with protected peptide Fragment II;
   (b) deprotecting the Fmoc-protecting group of the resulting peptide of step (a) and coupling it with protected Fragment III;
   (c) deprotecting the Fmoc-protecting group of the resulting peptide of step (b) and coupling it with protected Fragment IV;
   (d) deprotecting the resulting protected peptide of step (c) to yield deprotected Ac(1–31)-NH$_2$.

2. The method of claim 1, further comprising purifying the deprotected peptide Ac(1–31)-NH$_2$.

3. The method of claim 2, wherein purification is accomplished via preparative HPLC.

4. A method for the synthesis of a purified compound Ac-(1–31)-NH$_2$ (SEQ ID NO:1) by coupling four Fmoc protected peptide fragments peptide Fragment I (SEQ ID NO:2), peptide Fragment II (SEQ ID NO:3), peptide Fragment III (SEQ ID NO: IV) and peptide Fragment IV (SEQ ID NO:5), said method comprising:
   (a) deprotecting the Fmoc-protecting group of peptide Fragment I;
   (b) coupling the deprotected peptide Fragment I with protected peptide Fragment II yielding protected intermediate Fmoc(19–31)-NH$_2$;
   (c) deprotecting the Fmoc-protecting group of intermediate Fmoc(19–31)-NH$_2$;
   (d) coupling the deprotected intermediate Fmoc(19–31)-NH$_2$ with protected Fragment III yielding protected intermediate Fmoc(9–31)-NH$_2$;
   (e) deprotecting the Fmoc-protecting group of intermediate Fmoc(9–31)-NH$_2$;
   (f) coupling the deprotected intermediate Fmoc(9–31)-NH$_2$ with protected Fragment IV yielding protected intermediate Ac-(1–31)-NH$_2$;
   (g) deprotecting the protected peptide Ac(1–31)-NH$_2$; and
   (h) purifying the deprotected peptide Ac(1–31)-NH$_2$.

5. The method of claim 4, wherein purification in step (h) is accomplished via preparative HPLC.

6. The method of claim 4 wherein said Fmoc-protecting group of said peptide fragments and intermediates is deprotected with 10% Et$_2$NH in DMF.

7. The method of claim 4 wherein after deprotection, fluorene is removed by washing said peptide fragments and intermediates with hexane-ether.

8. The method of claim 4, wherein said deprotected peptide fragments and intermediates are
   a) coupled with 1.0 equivalent of said protected peptide fragments using HBTU, HOBt in DMF-CH$_2$Cl$_2$ using DIPEA;
   (b) evaporated and dissoluted in CH$_2$Cl$_2$; and
   (c) extracted with saturated NaHCO$_3$ and 10% citric acid.

9. The method of claim 8, wherein said coupling is performed at 0°/30 minutes-1 hour and 25°/3 hours with 1.2 eq of HBTU, 3.6 eq HOBt and 4.8 eq of DIPEA.

* * * * *